(12) United States Patent
Öberg

(10) Patent No.: US 6,476,009 B1
(45) Date of Patent: *Nov. 5, 2002

(54) METHOD FOR CONTROL AND TREATMENT OF ACQUIRED IMMUNODEFICIENCY SYNDROME (AIDS)

(75) Inventor: Bo Fredrik Öberg, Askvägen (SE)

(73) Assignee: Astra Lakemedel Aktiebolag, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 08/484,383

(22) Filed: Jun. 7, 1995

Related U.S. Application Data

(63) Continuation of application No. 08/168,914, filed on Dec. 16, 1993, which is a continuation of application No. 07/809,848, filed on Dec. 18, 1991, now abandoned, which is a continuation of application No. 07/086,218, filed on Aug. 13, 1997, now abandoned, which is a continuation of application No. 06/793,576, filed on Oct. 31, 1985, now abandoned.

(51) Int. Cl.$^7$ ............................................. A61K 31/66
(52) U.S. Cl. ...................................................... 514/120
(58) Field of Search ........................................ 514/120

(56) References Cited

U.S. PATENT DOCUMENTS

| | | | | |
|---|---|---|---|---|
| 4,215,113 A | * | 7/1980 | Eriksson et al. | ............ 514/120 |
| 4,339,445 A | * | 7/1982 | Eriksson et al. | ............ 514/120 |

* cited by examiner

Primary Examiner—Jerome D. Goldberg
(74) Attorney, Agent, or Firm—White & Case LLP

(57) ABSTRACT

The present invention relates to a method of inhibiting the activity of the HIV virus in a human comprising administering to the human an effective dose of phosphonoformic acid or a therapeutically effective salt thereof.

5 Claims, No Drawings

METHOD FOR CONTROL AND TREATMENT OF ACQUIRED IMMUNODEFICIENCY SYNDROME (AIDS)

This application is a continuation of application Ser. No. 08/168,914, filed on Dec. 16, 1993, which is a continuation of application Ser. No. 07/809,848, filed Dec. 18, 1991 (abandoned), which is a continuation of application Ser. No. 07/086,218, filed Aug. 13, 1987 (abandoned), which is a continuation of application Ser. No. 06/793,576, filed Oct. 31, 1985 (abandoned).

FIELD OF THE INVENTION

The present invention relates to a method for the therapeutical and prophylactic control and treatment of acquired immunodeficiency syndrome (AIDS).

BACKGROUND OF THE INVENTION

In the late seventies a new disease was reported, which subsequently was referred to as Acquired Immuno Deficiency Syndrom (AIDS). It is now generally accepted that a retrovirus referred to as Human T-cell Leukemia Virus (HTLV-III) or Lymphadenopathy Associated Virus (LAV) plays an essential role in the etiology of AIDS. This virus will herebelow be denoted HTLV-III.

The full-blown AIDS is characterized by a profound immunodeficiency due to low numbers of a subset of lymphocytes-T-helper cells, which are the targets for HTLV-III lytic infections. The profound immunodeficiency, in the full-blown AIDS patients makes these patients highly susceptible to a variety of opportunistic infections of bacterial, fungal, protozoal or viral etiology. The etiological agents among viral opportunistic infections are often found in the herpes virus group, i.e., Herpes Simplex virus (HSV), Varicella Zoster virus (VZV), Epstein-Barr virus (EBV) and especially cytomegalo virus(CMV).

The discovery of HTLV-III as the likely cause of AIDS has presented a possible target for chemotherapy.

DETAILED DESCRIPTION OF THE INVENTION

It has now been found, according to the present invention, that he compound phosphonoformic acid, or a therapeutically acceptable salt thereof has unobvious and beneficial properties as an agent capable of inhibiting the activity of the HTLV-III virus in mammals and man.

The compound phosphonoformic acid, which in the form of its trisodium salt is known as foscarnet, is described i.a. in U.S. Pat. No. 4,215,113 and U.S. Pat. No. 4,339,445 as an antiviral agent, and in particular as an agent with an antiviral activity against the herpesvirus group (HSV-1, HSV-2, VZV, EBV and CMV). The antiviral activity of foscarnet against herpesviruses, and in particular against cytomegalo virus (CMV), is an additional advantageous property in the treatment of AIDS, since CMV infection is one of the most common and most serious opportunistic infections afflicting AIDS patients and since the activation of B cells by CMV might be a cofactor in the development of AIDS.

In clinical practice phosphonoformic acid will preferably be used in the form of its trisodium salt, although other physiologically acceptable salts may be used as is described in U.S. Pat. No. 4,215,113. Thus, such suitable salts are e.g. amine salts, e.g. dimethylamine and triethylamine salt, ammonium salt, tetrabutylammonium salt, cyclohexylamine salt, dicyclohexylamine salt; and metal salts, e.g. mono-, di- and tripotassium salt, magnesium salt, calcium salt and zinc salt.

In clinical practice the phosphonoformic acid will normally be administered orally, intranasally, by injection, by infusion or by inhalation in the form of a pharmaceutical preparation comprising the active ingredient in the form of the original compound or optionally in the form of a pharmaceutically acceptable salt thereof, in association with a pharmaceutically acceptable carrier which may be a solid, semi-solid or liquid diluent or an ingestible capsule. The compound may also be used without carrier material, As examples of pharmaceutical preparations may be mentioned tablets, granulates which can be ingested as such, drops such as nasal drops, suspensions, aerosols for inhalation, nasal spray, liposomes, solutions etc. Usually the active substance will comprise between 0.05 and 99, or between 0.1 and 99% by weight of the preparation, for example between 0.5 and 20% for preparations intended for injection and between 0.1 and 99% for preparatons intended for oral administration. To produce pharmaceutical preparations in the form of dosage units for oral application the active ingredient may be mixed with a solid, pulverulent carrier, for example lactose, saccharose, sorbitol, mannitol, a starch such as potato starch, corn starch, amylopectin, laminaria powder or citrus pulp powder, a cellulose derivative or gelatine and also may include lubricants such as magnesium or calcium stearate or a Carbowax® or other polyethylene glycol waxes and compressed to form tablets or cores for dragees. If dragees are required, the cores may be coated for example with concentrated sugar solutions which may contain gum arabic, talc and/or titanium dioxide, or alternatively with a film forming agent dissolved in easily volatile organic solvents or mixtures of organic solvents. Dyestuffs can be added to these coatings, for example, to distinguish between different contents of active substance. For the preparation of soft gelatine capsules consisting of gelatine and, for example, glycerol as a plasticizer, or similar closed capsule, the active substance may be admixed with a Carbowax® or a suitable oil as e.g. sesame oil, olive oil, or arachis oil. Hard gelatine capsules may contain granulates of the active substance with solid, pulverulent carriers such as lactose, saccharose, sorbitol, mannitol, starches (for example potato starch, corn starch or amylopectin), cellulose derivatives or gelatine, and may also include magnesium stearateor stearic acid as lubricants.

By using several layers of the active drug, separated by slowly dissolving coatings sustained release tablets are obtained. Another way of preparing sustained release tablets is to divide the dose of the active drug into granules with coatings of different thicknesses and compress the granules into tablets together with the carrier substance. The active substance can also be incorporated in slowly dissolving tablets made for instance of fat and wax substances or evenly distributed in a tablet of an insoluble substance such as a physiologically inert plastic substance.

In order to obtain dosage units for oral preparations—tablets, capsules etc.—which are designed so as to prevent release of and possible decomposition of the active substance in the gastric juice, the tablet, dragees etc. may be enteric-coated, that is provided with a layer of a gastric juice-resistant enteric film or coating having such properties that it is not dissolved at the acidic pH in the gastric juice. Thus, the active substance will not be released until the preparation reaches the intestines. As example of such known enteric coatings may be mentioned cellulose acetate phtalate, hydroxypropylmethylcellulose phtalates such as those sold under the trade names HP 50, and Edragit®L and Eudragit®S.

Effervescent powders are prepared by mixing the active ingredient with non-toxic carbonates or hydrogen carbonates of e.g. sodium, potassium or calcium, such as calcium carbonate, potassium carbonate and potassium hydrogen carbonate, solid, non-toxic acids such as tartaric acid, ascorbid acid, and citric acid, and for example aroma.

Liquid preparations for oral application may be in the form of elixirs, syrups or suspensions, for example solutions containing from about 0.1% to 20% by weight of active substance, sugar and a mixture or ethanol, water, glycerol, propylene glycol and optionally aroma, saccharine and/or carboxymethylcellulose as a dispersing agent.

For parenteral application by injection preparations may comprise an aqueous solution of a water soluble pharmaceutically acceptable salt of phosphonoformic acid desirably in a concentration of 0.5–10%, and optionally also a stabilizing agent and/or buffer substances in aqueous solution. Dosage units of the solution may advantageously be enclosed in ampoules.

In the treatment of AIDS patients, it will be preferred to administer foscarnet parenterally, via the intravenous route, or orally. The dosage at which the active compound is administered may vary within a wide range and will depend on various factors such as the severity of the infection, the age of the patient, etc., and may have to be individually adjusted. As a possible range for the amount of foscarnet which may be administered parenterally per day may be mentioned 5–20 g, especially about 15 g. As a possible range for the amount of foscarnet which may be administered per day at oral administration may be mentioned 5–50 g. It is desirable to administer an amount of foscarnet which gives a serum level of phosphonoformic acid in the range 50–1000 $\mu$M, especially 300–600 $\mu$M. The serum level 450 $\mu$M may be regarded as on average especially desirable. That level will normally be sufficient to inhibit HTLV-III virus as well as CMV virus.

A preferred parenteral composition for intravenous infusion is as follows:

Foscarnet (trisodium phosphonoformate hexahydrate 24.7 mg
Hydrochloric acid 2M for injection q.s. to pH 7.4
Water for injection, to 1.0 ml.

The treatment of AIDS patients with foscarnet may have to be continued for a period of 1–4 or preferably 2–4 weeks or longer, depending on the individual case.

In order to achieve fast a steady state serum level of phosphonoformic acid it may be preferred at intravenous administration to administer and initial bolus dose of from 9 mg/kg to 20 mg/kg over 10 to 30 minutes. It is preferred to have a steady state plasma level of foscarnet at about 150 $\mu$g/ml (450 $\mu$M).

In the following, test data on the effect of foscarnet on HTLV-III viral functions will be given.

MATERIALS AND METHODS

Source of HTLV-III Reverse Transcriptase and Assay Conditions. HTLV-III reverse transcriptase used in these studies was purified by sequential chromatography on DEAE, cellulose, phosphocellulose and hydroxyapatite. The purified anzyme was stored in 50 mM Tris-HCl (pH 7.5), 1 mM dithiothreitol (DTT), 0.01% Triton X-100 and 20% glycerol. Reverse transcriptase assays were carried out in a reaction mixture (50 $\mu$l) containing 50 mM Tris-HCl (pH 7.5), 5 mM DTT, 100mM potassium chloride, 0.01% Triton X-100 or NP40, 10 $\mu$g/ml (dT)$_{15}$.(A)$_n$ as template primer and/$^3$H/deoxythymidine triphosphate (/$^3$H/-dTTP). The reaction mixture was incubated for 1 hour at 37°, and the reaction was stopped by the addition of 50 $\mu$g of yeast tRNA and 2 ml of 10% solution of trichloroacetic acid (TCA) containing 1 mM sodium pyrophosphate. The samples were filtered on millipore filters (0.45 $\mu$m), washed first with 5% TCA solution (5 times) and then with 2 ml of 70% ethanol. The filters were dried under a heat lamp, scintillation fluid was added and the radioactivity counted in a $\beta$-scintillation counter.

HTLV-III Infection of H9 Cells. H9 cells constitute a human cell line that can be chronically infected with HTLV-III virus. (Science 1984; 224: 497–500). H9 cells were treated with polybrene (2 $\mu$g/ml) for 30 min. at 37° C., washed free of polybrene and infected with 2×10$^8$ HTLV-III virus particles per 4×10$^5$ H9 cells. The positive control sample did not receive any drug whereas the test samples received various concentratons of foscarnet. The cultures were analyzed for HTLV-III reverse transcriptase activity as described above.

RESULTS

The effect of foscarnet on purified HTLV-III reverse transcriptase (RT) was assayed as a function of drug concentration.

The concentration of foscarnet causing 50% inhibition of HTLV-III reverse transcriptase activity from different virus isolates was found to be between 0.1 $\mu$M and 2 $\mu$M. Similar results were obtained when the effect of foscarnet was studied on the endogenous reverse transcriptase activity of the disrupted virus in the absence of an exogenously added template-primer such as (dT)$_{15}$. (A)$_n$. The inhibition of reverse transcriptase by foscarnet has been shown to be noncompetitive with respect to substrate and uncompetitive with respect to template.

The effect of foscarnet on the replication of HTLV-III in H9 cells was determined as a function of both foscarnet concentration and time of incubation. The degree of inhibition is dependent on both the time of incubation and the foscarnet concentration and an inhibition of 50% was seen at 50 $\mu$M foscarnet after 6 days of incubation. A concentration of 300 $\mu$M was sufficient to obtain more than 95% inhibition after six days of incubation.

Foscarnet inhibits cell-growth by 50% at concentrations of about 1000 $\mu$M in a variety of cell types and this inhibition is reversible. Even when stationary cells are treated with 10 mM foscarnet, normal cell growth can be seen after removal of the drug. Uninfected H9 cells showed less than 50% inhibition at 750 $\mu$M foscarnet and more pronounced inhibition at higher concentrations.

Foscarnet has previously been evaluated clinically as a topical formulation against labial and genital herpes and found to be active and well tolerated. It has also been given by infusion to more than 250 patients with severe herpesvirus infections mainly caused by cytomegalovirus (CMV). These patients were given foscarnet intravenously by constant infusion for 1–4 weeks and, at steady state, serum levels of foscarnet reached in most cases were 300–450 $\mu$M (100–150 $\mu$g/ml). There were clear indications of a beneficial effect in patients treated with this drug.

Due to its non-competitive and direct mode of action, it appears that the sensitivity of HTLV-III to foscarnet in cell culture may be predictive of its effect against virus replication in vivo. It is thus possible to give foscarnet to patients at serum concentrations that will block HTLV-III replication and subsequent infection of T helper cell population. This applies in particular to pre-AIDS patients, that is patients who have not progressed to fully developed AIDS and who still have immune system capable of cooperating with an antiviral drug. A further advantage is a concomitant inhibition by foscarnet of CMV and EBV which is likely to occur.

Thus it is seen that foscarnet has clear and unobvious properties as an agent for use in the therapeutical or prophylactic control and treatment of AIDS and in the treatment also of pre-AIDS stages wherein both cases CMV and EBV might enhance the progress of the disease.

It may be desirable and is within the scope of the present invention to use foscarnet in combination with other therapeutical agents in the control and treatment of AIDS.

It is contemplated that such derivatives of phosphonoformic cid which are transformed in vivo to phosphonoformic acid in the mammal and human organism are included within the scope of the present invention. Thus for example those derivatives of foscarnet which are disclosed in U.S. Pat. Nos. 4,372,894 and 4,386,081 and which are esters of foscarnet are included in the scope of the present invention. The said two U.S. Pat. Nos. 4,372,894 and 4,386,081 are hereby incorporated by reference in the present specification.

What I claim is:

1. A method of inhibiting the activity of the HIV virus in a human comprising administering to the human an effective dose of phosphonoformic acid or a therapeutically effective salt thereof.

2. The method of claim 1, wherein the phosphonoformic acid or therapeutically acceptable salt thereof is administered in an amount sufficient to give a serum level of phosphonoformic acid in the range of 50–1000 $\mu$m.

3. The method of claim 1 or 2 wherein the phosphonoformic acid or therapeutically effective salt thereof is administered orally.

4. The method of claim 1 or 2 wherein the phosphonoformic acid or therapeutically effective salt thereof is administered parenterally.

5. The method of claim 1 or 2 wherein the therapeutically effective salt is the trisodium salt of phosphonoformic acid.

* * * * *